(12) United States Patent
Chuang et al.

(10) Patent No.: US 6,541,653 B2
(45) Date of Patent: Apr. 1, 2003

(54) SYNTHESIS OF CARBAMATE THROUGH LOW PRESSURE HETEROGENEOUS OXIDATIVE CARBONYLATION OF AMINES

(76) Inventors: Steven S. C. Chuang, 21 Nathan Ct., Hudson, OH (US) 44236; Yawu Chi, 33 Highland Glenn Dr., Apt. #115, Randolph, MA (US) 02368; Bei Chen, 416 Allyn St., Akron, OH (US) 44304; Pisanu Toochinda, 274 Wheeler St., Apt. #1, Akron, OH (US) 44304

( * ) Notice: Subject to any disclaimer, the term of this patent is extended or adjusted under 35 U.S.C. 154(b) by 0 days.

(21) Appl. No.: 09/843,045

(22) Filed: Apr. 26, 2001

(65) Prior Publication Data

US 2002/0183541 A1 Dec. 5, 2002

(51) Int. Cl.$^7$ ............................................. C07C 261/00
(52) U.S. Cl. .............................. 560/24; 560/32; 560/33; 560/50; 560/115; 560/157
(58) Field of Search .............................. 560/24, 32, 33, 560/50, 115, 157

(56) References Cited

U.S. PATENT DOCUMENTS

| 4,621,149 A | * | 11/1986 | Shinsuke et al. | ............... | 560/24 |
|---|---|---|---|---|---|
| 4,705,883 A | | 11/1987 | Grate et al. | ................... | 560/25 |
| 4,976,679 A | | 12/1990 | Okawa et al. | ............... | 560/190 |
| 5,008,435 A | * | 4/1991 | Kuo-Liang et al. | ............ | 560/24 |
| 5,962,721 A | | 10/1999 | Kim et al. | .................... | 560/24 |

OTHER PUBLICATIONS

The Merck Index, 9th Ed., (1976), pp. 855, 1155–1156.*
Kirk–Othmer, Encyclopedia of Chemical Technology 4th Ed. (1996), vol. 20, pp. 1007–1059.*

"An Exceptionally Mild, Catalytic Homogeneous Method for the Conversion of Amines into Carbamate Esters" by Howard Alper and Frederick W. Hartstock, *J. Chemical Soc., Chemical Communication*, pp. 1141–1142 (1985).
"A Novel Catalytic Synthesis of Carbamates by the Oxidative Alkoxycarbonylation of Amines in the Presence of Plantinum Group Metal and Alkali Metal Halide or Onium Halide" by Fukuoka et al., *J Org. Chem.*, vol. 49, pp. 1458–1460 (1984).
"Oxidative Carbonylation of Aniline Over Pd/C Catalyst: Effect of Promoters, Solvents, and Reaction Conditions" by Sunil P. Gupte and Raghunath V. Chaudhari, *Journal of Catalysis*, vol. 114, pp. 246–258 (1988).
Novel Catalytic Synthesis of Carbamates by the Oxidative Alkoxycarbonylation of Amines in the Presence of Palladium and Iodide by Fukuoka et al., *J. Chemical Soc., Chemical Communication*, pp. 399–400 (1984).
"Indirect Electrochemical Carbonylation of Aromatic Amines With a Palladium Catalyst" by Hartstock et al., *Tetrahedron Letters*, vol. 35 (47), pp. 8761–8764, (1994).

* cited by examiner

*Primary Examiner*—Paul J. Killos
(74) *Attorney, Agent, or Firm*—Renner, Kenner, Greive, Bobak, Taylor & Weber (57) ABSTRACT

The process disclosed herein satisfies the need in the art for an industrially viable oxidative carbonylation catalytic system, and is capable of producing carbamates at a significantly higher rate than those processes reported in journal and patent literature. This reaction process takes place via a reaction mechanism that does not involve drastic conditions. Specifically, the catalytic system of the present invention employs Group VIII metal catalysts and/or copper-based catalysts with halide promoters to produce carbamates through heterogeneous oxidative carbonylation at atmospheric pressure and relatively non-drastic temperatures in a gas-solid carbonylation process.

15 Claims, 5 Drawing Sheets

SYNTHESIS OF CARBAMATE THROUGH LOW PRESSURE HETEROGENEOUS OXIDATIVE CARBONYLATION OF AMINES

BACKGROUND OF THE INVENTION

The present invention relates generally to the synthesis of carbamate and, more particularly, to the synthesis of carbamate and isocyanate through the heterogeneous oxidative carbonylation of amines using copper-based catalysts and/or Group VIII metal-based catalysts.

Isocyanates are important intermediates in the manufacture of pesticides, polyurethane foam plastics, synthetic leather, adhesives, and coatings. Currently, isocyanates are commonly produced by a phosgene-amine reaction, although considerable efforts have been devoted to developing a new phosgene-free route. An alternative, phosgene-free route is desirable because phosgene is highly toxic, making the production process inherently unsafe and significantly increasing the manufacturing cost of isocyanates.

One promising alternative approach that has been the subject of research in recent years involves the oxidative carbonylation of amines to carbamate followed by thermal decomposition of the carbamate to isocyanate. So far, Group VIII metals and/or copper-based catalysts with halide promoters have reportedly been the most active catalysts for oxidative carbonylation of amines. However, although effective, these prior art catalysts usually require drastic reaction conditions. Typical reactions are carried out at temperatures from about 373 to about 483 K and under pressure from about 2 MPa to about 8 MPa. These severe conditions, especially the significant pressure required, frustrate the use of these catalysts in an industrial setting.

Additionally, prior art processes for the production of carbamate are carried out through a liquid-solid carbonylation process in which solid catalyst is immersed in liquid reactant(s). These processes require high pressures to enable gaseous reactants to reach and react with the catalyst by dissolving into the liquid reactant(s). Also these processes require an involved separation step for recovering the catalyst from the desired product. Developing a new catalytic system that can work at mild conditions and without the need for employing complex separation techniques is a focus of the present invention.

The oxidative carbonylation of amines to carbamate esters catalyzed by a palladium group metal and iodide ion is disclosed in two closely related articles, namely, *J Org. Chem.* 1984, 49, 1458 and *J Chem. Soc., Chem. Commun.*, 1984, 399, both by Fukuoka and co-workers. They taught that oxidative carbonylation carried out in the presence of these catalysts required a pressure of about 8.3 MPa, which, as mentioned above, is undesirably high for the mass production of carbamates in an industrial setting.

Fukuoka and co-workers studied a liquid-solid carbonylation process in which solid Pd catalyst and solid iodide source are added to liquid alcohol in an autoclave. Carbon monoxide (CO) and oxygen ($O_2$) are pressurized into the autoclave so as to become dissolved in the liquid reagents, in order to reach and react with alcohol and amine on the catalyst. While somewhat effective, this reaction necessarily entails the involved step of catalyst recovery. Particularly, the solid Pd catalyst must be recovered from the carbamate product produced, and, in an industrial setting, this is no easy task. To recover the catalyst, process steps, such as distillation and extraction, must be employed.

Alper and Hartstock, *J. Chem. Soc., Chem. Commun.* 1141 (1985), disclose catalytic systems including palladium chloride, copper chloride and hydrochloric acid to produce carbamates from amines. This Wacker-type catalytic system, consisting of $PdCl_2$—$CuCl_2$-HCl, is disclosed as being effective at mild conditions (1 atm and room temperature) in the oxidative carbonylation of amines to produce a high yield of carbamate. In this system carbon monoxide (CO) and oxygen ($O_2$) are bubbled through alcohol to which is added, in sequence, $PdCl_2$, hydrochloric acid, $CuCl_2$, and amine. The mixture is stirred overnight, at ambient temperature and pressure, and filtered, and the filtrate is subjected to rotary evaporation. The resulting oil is treated with either diethyl ether or acetone and filtered, and concentration of the filtrate yields the carbamate ester. Further purification is affected by thin-layer or column chromatography (silica gel). Thus, as with the process disclosed by Fukuoka and co-workers, a somewhat complex separation step is involved.

Gupte and Chaudhari, *Journal of Catalysis* 114, 246–258 (1988), studied the oxidative carbonylation of amines using a Pd/C—NaI catalytic system. Although effective at producing carbamates, this catalytic system requires the use of high pressures.

The oxidative carbonylation experiments are carried out in a 3 00 $cm^3$ capacity, high-pressure, stirred autoclave. A known quantity of aniline, catalyst, 5% Pd/C, NaI and alcohol solvent are charged into the autoclave. The autoclave is pressurized with carbon monoxide and oxygen to a total pressure of 4.1 MPa. The contents are heated and the reaction started by switching on the stirrer. The reaction is carried out at a constant pressure by supplying a $CO:O_2$ mixture (2:1 ratio) from a reservoir. After two hours, the contents are cooled and products analyzed. The process taught by Gupte and Chaudhari involves liquid-solid carbonylation and therefore requires the burdensome step of separating catalyst from the carbamate product produced.

U.S. Pat. No. 4,976,679 to Okawa et. al. discloses a process for producing carbamate that comprises reacting a primary amine, an organic compound containing a hydroxyl group or groups (e.g. alcohol), carbon monoxide, and molecular oxygen in the presence of catalytic systems containing at least one member selected from copper and copper-containing compounds and at least one halogen selected from iodine, chlorine, and bromine. Thus, Okawa discloses that expensive palladium group metals are not necessary catalysts for the oxidative carbonylation of amines to carbamates. Okawa does, however, teach the process as being carried out in a sealed autoclave wherein the catalyst and amine are placed in the alcohol, and carbon monoxide and air are added to the autoclave and subjected to pressure so as to dissolve in the alcohol and therefore reach and react with the catalyst.

While various processes and catalytic systems for the oxidative carbonylation of amines to carbamates are known, these prior art processes have concentrated on the liquid-solid carbonylation process in solvent, and entail the involved step of separating the catalyst employed from the carbamate produced. This separation step is particularly burdensome in an industrial setting. Furthermore, it takes more than 1 hour for these prior art processes to achieve the desired conversion of reactants and desired yields in a batch mode. Thus, there exists a need in the art for an oxidative carbonylation process converting amines to carbamates at non-drastic conditions, at an appropriate reaction rate, without the need for involved separation techniques to recover the carbamate produced from the catalyst employed.

DISCLOSURE OF THE INVENTION

The process disclosed herein satisfies the need in the art for an industrially viable oxidative carbonylation catalytic system, and is capable of producing carbamates at a significantly higher rate than those processes reported in journal and patent literature. This reaction process takes place via a reaction mechanism that does not involve drastic conditions. Specifically, the catalytic system of the present invention employs Group VIII metal catalysts and/or copper-based catalysts with halide promoters to produce carbamates through heterogeneous oxidative carbonylation at atmospheric pressure and relatively non-drastic temperatures in a gas-solid carbonylation process.

The present invention provides a method for the synthesis of carbamate through gas-solid oxidative carbonylation. Advantageously, this heterogeneous process can be carried out at non-drastic conditions and without the need for a subsequent catalyst recovery step. Various catalytic systems, whether known or heretofore unknown in the art, may be employed. Such catalyst systems may include copper-based catalysts, Group VIII metal-based catalysts, or co-catalytic systems including one or more Group VIII metal-based catalyst and/or one or more copper-based catalyst.

In general, the present invention provides a gas-solid carbonylation process for the production of carbamate ester. This process involves reacting, in the gaseous state, an amine, alcohol, oxygen, and carbon monoxide in the presence of a solid catalytic system including at least one catalyst of the formula $M_nX_m$ and at least one alkali salt of the formula AZ, wherein M is copper or Group VIII metal, X is a halogen or oxygen, n and m are whole numbers dependent upon the balancing of the valence numbers of M and X, A is an alkali metal, and Z is a halogen.

PREFERRED EMBODIMENT FOR CARRYING OUT THE INVENTION

In the process of the present invention, carbamates are produced through a gas-solid carbonylation process. Advantageously, this heterogeneous oxidative carbonylation process can be carried out at atmospheric pressure and relatively non-drastic temperatures and, notably, does not require an involved separation technique for recovery of the carbamates from the catalysts employed. By "heterogeneous" it is meant that the process involves more than one phase such that the catalyst and reactants are not in the same phase, particularly, where the reactants are in the gas phase and the catalyst is in the solid phase. As will be taught herein, this gas-solid carbonylation process may be carried out in a continuous or batch mode. Preferably, it is carried out in a continuous mode.

The process of the present invention involves reacting a primary amine, an organic compound containing at least one hydroxyl group, carbon monoxide, and molecular oxygen with one another in the presence of a catalytic system, wherein the reactive ingredients are in the gaseous state while the catalytic system is employed as a solid. Generally, the catalytic system includes at least one copper- or Group VIII metal-based catalyst, which may or may not be supported on a catalyst support, with an alkali salt.

Although the particulars of the reaction mechanism through which the process of the present invention operates it is not yet understood, the reaction itself can be represented by the following formula (I):

(I)

$$R^1NH_2 + CO + 1/2\, O_2 + R^2OH \xrightarrow{M_nX_m/AZ} R^1NHCOR^2 + H_2O$$
$$\phantom{R^1NH_2 + CO + 1/2\, O_2 + R^2OH \xrightarrow{M_nX_m/AZ} R^1NH}\underset{O}{\|}$$

wherein $R^1NH_2$ generally represents the primary amine, $R^2OH$ generally represents the organic compound containing at lease one hydroxyl group, $M_nX_m$ generally represents the at least one copper-based or Group VIII metal-based catalyst, and AZ generally represents the alkali salt.

The primary amine ($R^1NH_2$) reagent in the present invention may include aliphatic, aromatic, alicyclic, and heterocyclic compounds containing at least one amine group. Thus, $R^1$ may be selected from the group consisting of phenyl groups and alkyl groups having from one to sixteen carbon atoms (C1 to C16).

More particularly, the aromatic or heterocyclic amines may include, by way of non-limiting example, aniline, 1,2-diaminobenzene, 1,4-diaminobenzene, isomers of chloroaniline, 3,4-dichloroaniline, 4-isopropylaniline, p-toluidine, chlorotoluidine, xylidine, alkoxyamilines, isomers of nitroamiline, 2,3-diaminotoluene, 2-amino-4-nitrotoluene, 2-amino-3-nitrotoluene, 2-amino-5-nitrotoluene, aminophenols, diaminoxylene, aminonitroxylenes, aminonaphthalenes, amino-anthracenes, chloraminobenzoic acids, aminobenzenesulfonic acids, 4,4-diaminodiphenylmethane, 2,2-diaminodiphenylmethane, 2,4-diaminodiphenylmethane, tris(4-aminophenyl)methane, aminopyridines, aminoquinolines, aminopyrroles, aminofurans, aminothiophenes, and 2-aminobenzothiazoles.

The organic compound containing a hydroxyl group(s) ($R^2OH$) used in the present invention may include alcohols and phenols that have at least one OH group. Non-limiting examples of useful alcohols include methanol, ethanol, n-propanol, isopropanol, n -butanol, tert-butanol, n-pentanol, n-hexanol, cyclohexanol, benzyl alcohol, cycloethanol, ethylene glycol, diethylene glycol, propylene glycol, glycerol, and trimethylolpropane. Non-limiting examples of useful phenols, include phenol, naphthols, anthranol, phenanthrol, and hydroxybenzofurans.

As the molecular oxygen reagent, pure oxygen and air can be used either as they are or after being diluted with other gases that do not inhibit the reaction, for example, inert gases such as argon, helium, nitrogen, and carbon dioxide.

As the carbon monoxide reagent, there can be used pure carbon monoxide, and mixed gases of carbon monoxide and inert gases (as above).

As mentioned, the catalytic system of the present invention contains at least one catalyst of the general formula $M_nX_m$, which, optionally, may be provided on a catalyst support, and an alkali salt of the general formula AZ. The discussion below regarding the useful selections for components M, X, A, and Z served to define useful catalytic systems in accordance with the present invention.

In the at least one catalyst $M_nX_m$, M may be selected from copper or the Group VIII metals, while X may be selected from chlorine, bromine, iodine, or oxygen, with n and m being whole numbers dependent upon the balancing of the valence numbers for a given catalyst compound. When M is a Group VIII metal, an X component need not be provided.

The alkali salt is represented by AZ, wherein A is an alkali element and Z is a halogen. Non-limiting examples of particularly preferred alkali salts include NaCl, and NaI, NaBr, KI, KCl, KBr, and CsI.

The at least one catalyst may be provided on a catalyst support. Useful supports are well known in the art and may include, by way of non-limiting example, activated carbon; polymer supports such as poly(styrene-divinylbenzene), polystyrene, and polyimide; mesoporous materials such as zeolite, MCM-41, ZSM-5, HZSM-5, ammonium ZSM-5, and SBA-15; and metal oxides such as gamma-$Al_2O_3$, $SiO_2$, and $TiO_2$, and MgO. Catalyst supports are preferred because they provide high surface area to disperse active catalyst components and they immobilize the active catalyst components.

The catalytic systems according to the present invention may include either a single catalyst compound or multiple catalyst compounds satisfying the formula $M_nX_m$. Optionally, such solitary or co-catalysts may be provided on a catalyst support. Alkali salts are employed along with these catalysts to provide a catalytic system according to the present invention.

Non-limiting examples of useful solitary catalysts include Pd, $CuCl_2$, CuCl, and $PdCl_2$. As mentioned, these solitary catalysts can be provided on catalyst supports such as those mentioned above. Thus, non-limiting examples of useful supported catalysts including $CuCl_2$/HZSM-5, $PdCl_2$/HZSM-5, Pd/MCM-41, $CuCl_2$/MCM-41, $CuCl_2$/SBA-15, $PdCl_2$/SBA-15, $CuCl_2$/C and Pd/C.

Non-limiting examples of useful co-catalysts include $CuCl_2$—$PdCl_2$, $CuCl_2$—CuO, $CuCl_2$—$CuO_2$, CuCl—$PdCl_2$, and CuCl—$CuCl_2$. Such co-catalysts may be provided on catalyst supports such as those disclosed hereinabove. Non-limiting examples of useful supported co-catalysts include $CuCl_2$—$PdCl_2$/ZSM-5, $CuCl_2$—CuO/MCM-41, and $CuCl_2$—$CuO_2$/MCM-41.

Co-catalysts may also include three or more catalyst compounds satisfying the formula $M_nX_m$. It should also be appreciated by those of ordinary skill in the art that the alkali salt, in some instances, may be provided on a support.

The process according to the present invention is carried out in a gas-solid mode wherein the catalytic system is in the solid state and the reactants are caused to come into contact therewith while in the gaseous state. Various methods for carrying out the gas-solid carbonylation process of the present invention are disclosed below.

The present invention may be carried out in a continuous process. By way of non-limiting example, the process of the present invention can be carried out in a fixed bed reactor packed with a catalytic system according to the present invention as disclosed above. In a fixed bed process, a fixed bed reactor is packed with a catalytic system according to the present invention, and the carbon monoxide, oxygen, amine, and alcohol reagents are passed across the catalytic system within the fixed bed reactor while in the gaseous state.

The carbon monoxide and oxygen gaseous reactants are preferably used to carry evaporated gaseous amine and alcohol reactants to and through the fixed bed packed with the catalytic system.

The temperature and pressure within the fixed bed reactor are generally selected so as to maintain the reagents in the gaseous state during contact with the catalytic system. It will be appreciated that maintaining the reagents in the gaseous state requires carrying out the reaction below the saturated vapor pressures of the amine and alcohol. Particularly, the reaction temperature within the fixed bed reactor is preferably from about 323 K to about 543 K. In another embodiment of the present invention, the reaction temperature is preferably from about 383 K to about 483 K, and, in yet another embodiment, preferably, 433 K to 463 K. The reaction pressure is generally maintained at from about 0.1 MPa to about 5 MPa. In one embodiment of the present invention the reaction pressure is preferably from about 0.1 MPa to about 0.5 MPa. In another embodiment of the present invention, the reaction pressure is preferably 0.1 MPa to about 0.3 MPa, and, in yet another embodiment, preferably 0.1 MPa to about 0.12 MPa.

It should be readily appreciated by those of ordinary skill in the art that the temperature and pressure variables are selected and adjusted in light of the partial pressure of the various reagents while in their gaseous state. As long as all reactants are present in the fixed bed packed with the catalytic system, carbamate will be produced at the above mentioned reaction temperature and pressure. However, it is desirable to adjust the temperature and pressure of the reactant stream or streams and within the fixed bed to provide the reactants in the stoichiometric ratio as indicated in reaction (I) above. Thus, the reaction would be most efficient if the reactants were provided in a molar ratio of amine/CO/$O_2$/alcohol of 1/1/0.5/1, although, as the experiments hereinbelow show, such a ratio is not necessary for the production of the desired carbamate product. Indeed, to prevent the collection of solid carbamate on the catalytic surface, excess alcohol is desired. The carbamate will dissolve in the excess alcohol and be carried out of the presence of the catalytic system, where it can be isolated as will be described below.

It has been found that the reaction herein considered—a gas-solid carbonylation process—occurs more rapidly than the prior art liquid-solid carbonylation processes would suggest. Notably, while the prior art typically allowed for reaction times of about at least two hours, the gas-solid carbonylation process according to the present invention in a fixed bed reactor produces the desired carbamate product in about 10 minutes. Thus, the size of the fixed bed reactor and the flow rate of the reagents therethrough is selected so as to provide for a residence time of from about 5 minutes to about 60 minutes. In one embodiment of the present invention, the residence time within a fixed bed is preferably at least 5 minutes.

As indicated in reaction (I) provided above, carbamate and water are the products of the gas-solid carbonylation process of the present invention. These products may be collected by condensation as they exit the fixed bed reactor. The low solubility of carbamate in water results in phase separation, which allows separating of carbamate from water by decantation.

More particularly, it should be appreciated that the reaction considered herein, like most reactions in actual practice, is not 100% efficient and, therefore, any or all of the reactants may be present in the exit stream from the fixed bed. Thus, the potential compound exiting the fixed bed include carbon monoxide, oxygen, carbon dioxide (due to potential reaction between oxygen and carbon monoxide), amine, alcohol, carbamate, and water. As mentioned above, excess alcohol is preferably employed to ensure that the carbamate product is carried out in the presence of catalytic system. Of these potential exiting compounds, the gaseous CO, $CO_2$, and $O_2$ are easily withdrawn. The remaining compounds are condensed to the liquid phase and, therefore, may include amine, water, alcohol, and carbamate to dissolve in the alcohol. Due to its typically low boiling point, the alcohol may be evaporated off, thereby leaving crystallized carbamate behind in the remaining amine and water. The amine and water will typically be immiscible and the amine may be separated from the water to be recycled for use in producing more carbamate. The carbamate may easily be isolated by filtration.

Figure 1:
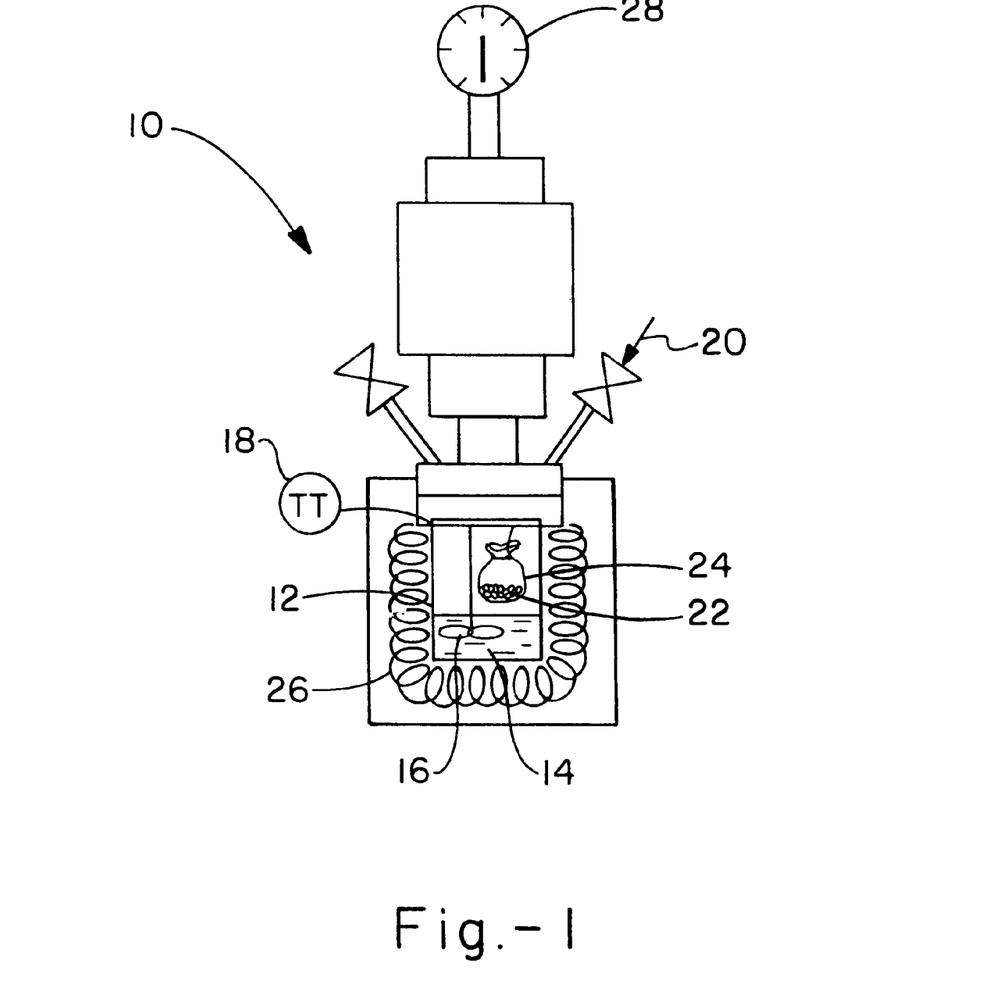
FIG. 1 is a schematic representation, in cross-section, of a batch reactor used for carrying out the process according to the present invention.

The present invention may also be carried out in a batch mode. Thus, by way of non-limiting example, the present invention may also be carried out in an autoclave. With reference to FIG. 1, it can be seen that such an exemplary batch mode reactor (autoclave) is designated generally by the numeral 10. Reactor 10 includes a reaction chamber 12 wherein the liquid reactants 14 are contained and mixed by stirrer 16. Reaction chamber 12 is maintained at an appropriate temperature by a thermocouple generally represented at numeral 18, and is pressurized by charging the gaseous reagents, CO and $O_2$, at gas inlet 20. Batch reactor 10 is adapted so as to suspend catalytic system 22 in reaction chamber 12, above and out of contact with liquid reactants 14. Although other devises and methods may be employed to separate the solid catalytic system 22 from the liquid reactants 14, in the present preferred embodiment, catalytic system 22 is simply suspended from the top of reaction chamber 12 by a gas permeable pouch 24. Notably, pouch 24 may be made from any material that will allow gaseous reagents to contact catalytic system 22 and yet will not deleteriously affect any of the reagents, catalyst components, or products produced under the reaction conditions.

Notably, the liquid reactants 14 consist of the alcohol and amine components of the reaction herein under study. The gaseous reactants, namely, oxygen and carbon monoxide, are fed to reaction chamber 12 at gas inlet 20. Again, the temperature and pressure within the reaction chamber 12 are selected so as to ensure that a sufficient amount of the liquid reactants 14 will evaporate to the gaseous state so as to reach catalytic system 22 along with the oxygen and carbon monoxide reagents so that the desired reaction will take place in a gas-solid carbonylation process. Temperature is maintained by heating coil 26, and pressure is measured by pressure gauge 28.

The temperature and pressure within the batch reactor are generally selected so as to maintain the reagents in the gaseous state during contact with the catalytic system. Particularly, the reaction temperature within the batch reactor is preferably from about 323 K to about 543 K. In another embodiment of the present invention, the reaction temperature is preferably from about 383 K to about 483 K, and, in yet another embodiment, preferably, 433 K to 463 K. The reaction pressure is generally maintained from about 0.1 MPa to about 5 MPa. In one embodiment of the present invention the reaction pressure is preferably from about 0.1 MPa to about 0.5 MPa. In another embodiment of the present invention, the reaction pressure is preferably 0.1 MPa to about 0.3 MPa, and, in yet another embodiment, preferably 0.1 MPa to about 0.12 MPa.

Generally, once all the gaseous (not shown) and liquid reactants 14 are charged to reaction chamber 12, and the proper temperature and pressure is maintained so as to ensure the presence of sufficient amounts of the various reactants within the gaseous state, the reaction is allowed to proceed for at least about 5 minutes and, more preferably, at least about 10 minutes.

EXPERIMENTAL

Figure 2:
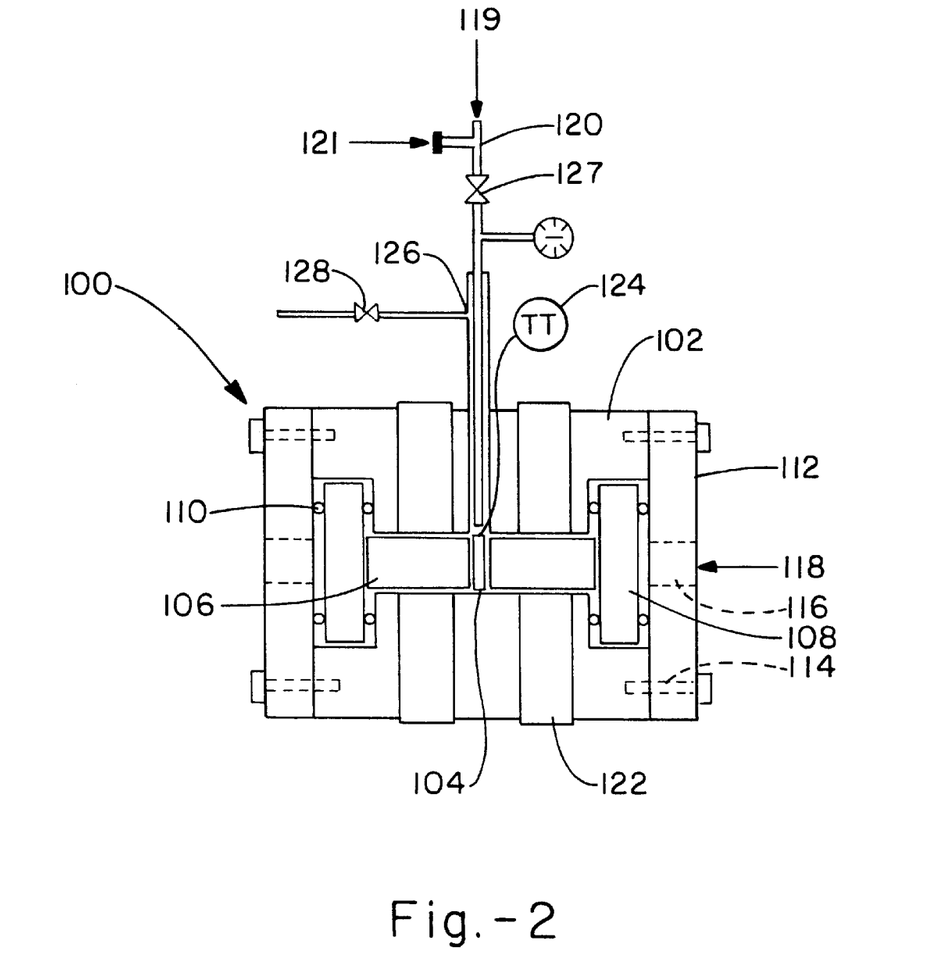
FIG. 2 is a schematic representation, in cross-section, of an infrared (IR) reactor cell used for carrying out the heterogeneous oxidative carbonylation process according to the present invention.

An infrared cell reactor was also employed in practicing the present invention, in order to quantify and qualify the reaction to show that the present gas-solid carbonylation process yields higher amine conversion than the liquid-solid carbonylation processes known in the prior art and also to show that the carbonylation reaction occurs quite rapidly. With reference to FIG. 2, an infrared cell reactor such as that employed in the present invention is designated generally by the numeral 100. Infrared cell reactor 100 includes a reactor cell 102 that retains a pressed catalyst disc 104 between $CaF_2$ rods 106 and $CaF_2$ windows 108, which are retained in place by o-rings 110. Reactor cell 102 is capped and access there to is provided by cover plates 112 and screws 114. Cover plates 112 include apertures 116, which are aligned with catalyst discs 104, $CaF_2$ rods 106, and $CaF_2$ windows 108. A beam of infrared light, generally represented by the arrow 118, is positioned so as to pass through the catalyst disc 104 and provide infrared spectra of absorbed species thereon. The gaseous and liquid reactants, generally represented by numerals 119 and 121, respectively, are fed into contact with catalyst disc 104 via inlet tube 120. Additionally, the system is pressurized and heated by heating tape 122 and the reaction temperature measure by a thermocouple generally represented at numeral 124. Inlet tube 120 is preferably partially surrounded by outlet tube 126, although other means for providing an outlet for the system may be employed. To close off reactor cell 102, inlet tube 120 and outlet tube 126 include on-off valves 127, 128, respectively.

Within infrared cell reactor 100, various catalytic systems may be tested by pressing them into catalyst discs 104, contacting them with the reactants. The results may then be qualified and quantified through analysis of the infrared spectra produced.

In order to demonstrate the practice of the present invention, the following examples have been prepared and tested as described hereinbelow. The examples should not, however, be viewed as limiting the scope of the present invention. The claims will serve to define the invention.

EXAMPLE 1

4.7 wt % $CuCl_2$-4.4 wt % $PdCl_2$/ZSM-5 was obtained by the sequential impregnation of $PdCl_2$ onto $CuCl_2$/ZSM-5, which was prepared by incipient wetness impregnation of $CuCl_2$ into H-ZSM-5. The catalyst was pressed in the form of a self-supporting disc weighing 25 mg and was placed in the IR beam path of the infrared cell reactor 100 as shown in FIG. 2.

Figure 3:
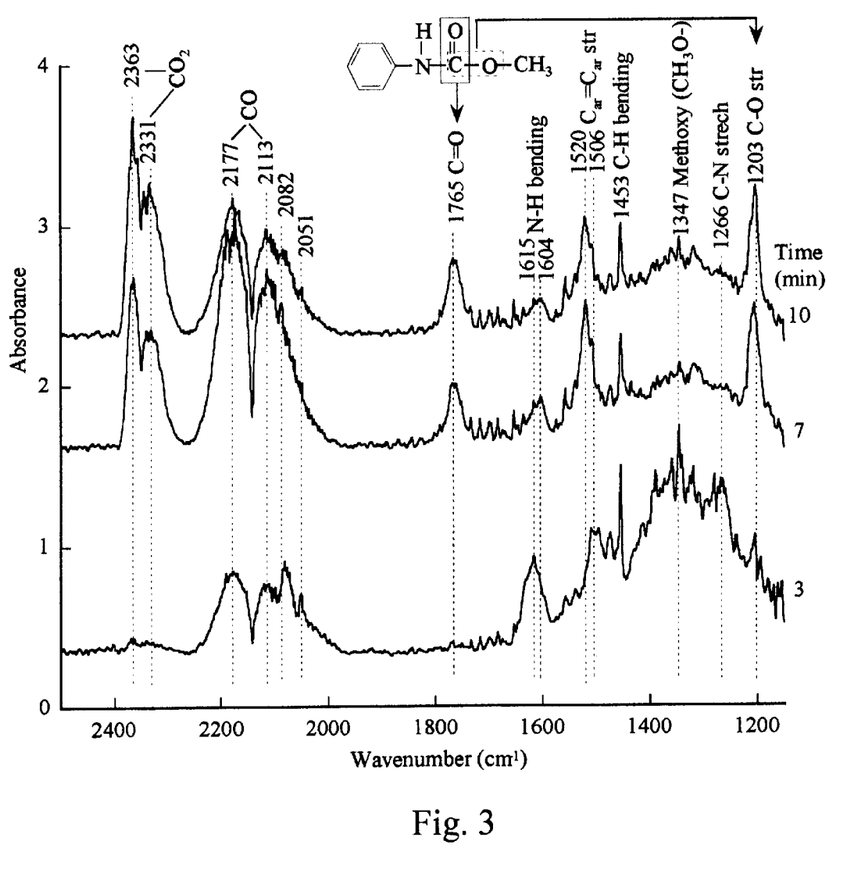
FIG. 3 is a IR spectra evidencing the production of carbamate according to Example 1 of the present invention, employing 4.7 wt % $CuCl_2$-4.4% $PdCl_2$/ZSM-5 and NaI as the catalytic system.

FIG. 3 shows IR spectra of adsorbed species on $CuCl_2$-$PdCl_2$/ZSM-5 taken during the reaction at 438 K and 0.101 MPa. The reagents were $CO/O_2$/aniline/methanol/NaI with amolar ratio of 8.07/0.81/17.1/79.3/3.6. Exposure of the catalyst to the reactants led to the appearance of linear CO at 2082 $cm^{-1}$ and 2051 $cm^{-1}$, N—H bending at 1615 and 1604 $cm^{-1}$, C=C stretch of the aromatic species at 1520 and 1506 $cm^{-1}$, C—H bending at 1453 $cm^{-1}$, methoxy ($CH_3O-$) at 1347 $cm^{-1}$, and C—N stretching at 1266 $cm^{-1}$. Increase in reaction time from 3 to 10 min led to a decrease of all the adsorbed reactant species and formation of $C_2$ at 2363 and 2331 cm$^{-1}$ as well as an increase in the C=O stretching (1765 cm$^{-1}$) and C—O stretching (1203 cm$^{-1}$) of the methyl phenyl carbamate species, suggesting that the carbamate species can be produced via the oxidative carbonylation of aniline with methanol at 0.101 MPa.

The rapid growth of the carbamate band in FIG. 3 demonstrates the high activity of CuCl$_2$—PdCl$_2$–NaI catalyst in oxidative carbonylation. Calibration of infrared intensity with known concentration of the reactant mixture showed the reaction resulted in an aniline conversion of 60% during the first 3 min and 70% following 10 min of the reaction with methyl phenyl carbamate as the only major product. The results of this study show that the reaction in the gas-solid mode gives higher rate of aniline conversion than that in the gas-liquid mode.

EXAMPLE 2

The 4.5 wt % CuCl$_2$-4.5wt %CuO$_x$/MCM-41 was prepared by a sequential incipient wetness impregnation method. This procedure consisted of: (i) impregnating MCM-4 1 powder with an aqueous solution of CuCl$_2$. 2H$_2$O, (ii) drying impregnated catalyst overnight in air at 298 K, (iii) calcinating the catalyst in flowing air from 298 K to 773 K at a rate of 3° C./min and then holding at 773 K for 12 h, for preparation of CuO/MCM-41 (iv) impregnating the CuO/MCM-41 with an aqueous solution of CuCl$_2$.2H$_2$O, and (v) drying the catalyst overnight at ambient conditions.

The MCM-41 was synthesized by mixing amorphous fumed silica, tetramethylammonium hydroxide, NaOH, NaAlO$_2$ cetyltrimethylammonium chloride, and deionized water in a molar ratio of 1/0.1/0.225/0.05/0.9/65.83. The mixtur es were stirred for 30 minutes and then held at 363 K under autogeneous pressure for 48 hours. The resulting precipitate was collected by filtration, washed thoroughly, and dried at room temperature. The surfactant was removed by calcination of precipitate in flowing air by heating from 298 K to 823 K at a rate of 2° C./min and holding at 823 K for 4–5 h. 30 mg of catalyst was pressed into a self-supporting disc and placed in the IR cell. The oxidative carbonylation was carried out with CO/O$_2$/methanol/aniline/NaI (molar ratio=5.8/0.58/102.6/7.611) at 438 K and 0.48 MPa for 8.45 min.

Figure 4:
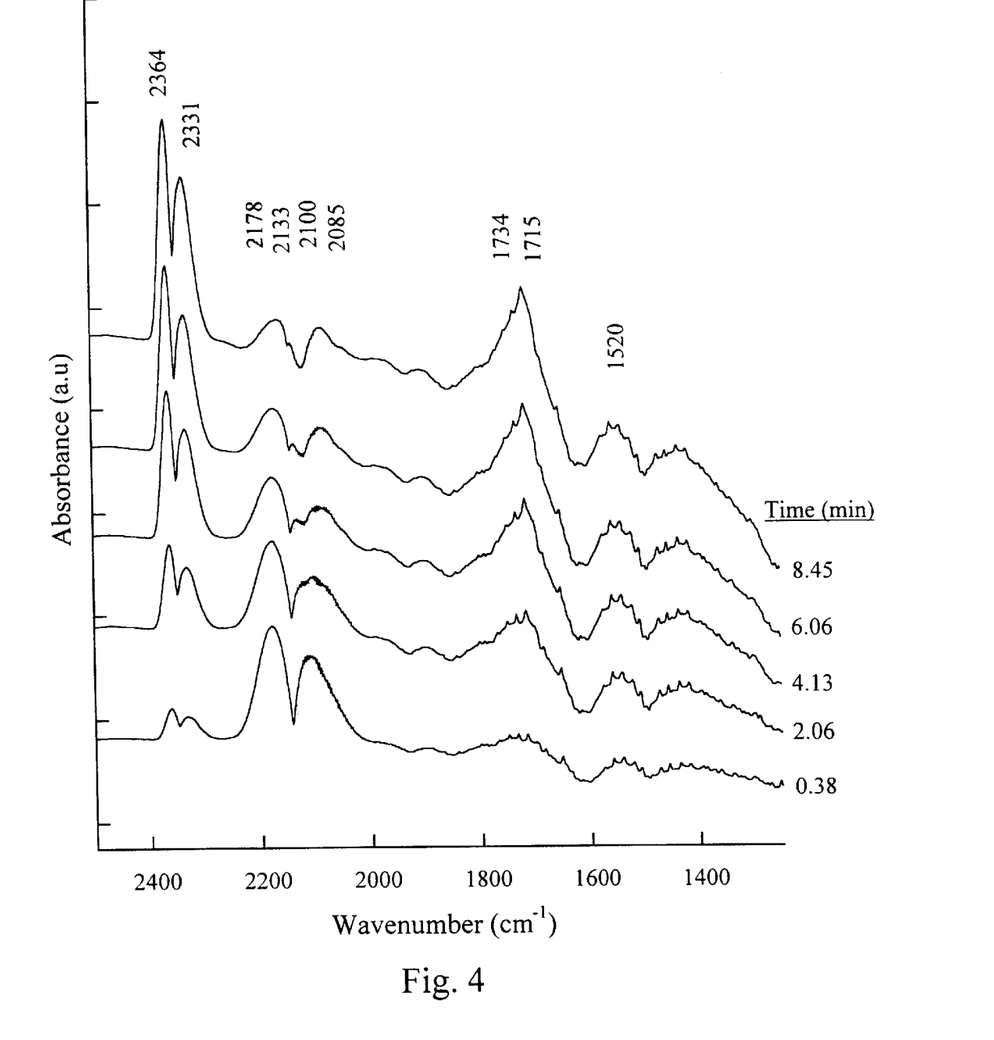
FIG. 4 is a IR spectra evidencing the production of carbamate according to Example 2 of the present invention, employing 4.5 wt % $CuCl_2$-4.5% CuO/MCM-41 1 and NaI as the catalytic system.

30 mg of catalyst was pressed into a self-supporting disk and placed in the IR cell. The oxidative carbonylation was carried out with CO/O2/methanol/aniline/ NaI (molar ratio– 5.8/0.58/102.6/7.6/1) at 438 K and 0.48 MPa for 8.45 min. FIG. 4 shows the infrared spectra of carbamate formation at 1734 and 1715 cm$^{-1}$ as well as the bands due to the linear gas CO at 2178 and 2100 cm$^{-1}$, and C=C stretching of aromatic species at 1520 cm$^{-1}$. The intensity of the carbamate and CO$_2$ by product increased with reaction time. Calibration of infrared intensity with known concentration of the reactant mixture showed the reaction resulted in a carbamate yield of 40.3% at 8.45 min

EXAMPLE 3

4.7 wt % CuCl$_2$-4.4 % PdCl$_2$/ZSM-5 was prepared by a sequential incipient wetness impregnation method. The preparation procedure consists of: (i) impregnation of ZSM-5 (Zeolyst International Product) with an aqueous solution of PdCl$_2$.2H$_2$O/HCl, (ii) impregnation of PdCl$_2$/ZSM-5 with an aqueous solution of CuCl$_2$.2H$_2$O, (iii) then drying overnight in air at the room temperature.

Seven hundred mg of PdCl$_2$—CuCl$_2$/ZSM-5 was loaded in a tubular reactor with the glass wool packed at both ends. The catalyst was exposed to a flow of CO/O$_2$ (molar ratio: 10/1) at 20 cm$^3$/min for 5 min. 0.2 cm$^3$ of methanol/aniline (molar ratio: 6:1) solution was injected into the CO/O$_2$ flow. The reaction was allowed to occur in a batch mode at 438 K for 6 min to produce methyl-N-phenyl carbamate. It should be appreciated that the present experiment was conducted in a "batch mode" by closing off the tubular reactor once the reactants had been introduced thereto. The batch mode as run only because practicalities at the laboratory prevented the use of a large amount of catalyst in a large tubular reactor. Thus, the small tubular reactor employed in this experiment, and in Example 4 hereinbelow, was closed off to provide for a sufficient reaction time, although, had the use of a larger tubular reactor and larger amounts of catalysts been practical, the same results could have been obtained by a continuous mode, wherein the flow rate of the reactants through the tubular reactor was adjusted to provide for the desired reaction time. The product was flushed by methanol and analyzed by gas chromatography (GC) to determine the compositions. GC results showed 5% aniline conversion and 100% carbamate selectivity.

EXAMPLE 4

5 wt % Pd-2.5%NaI—/C was prepared by sequential incipient wetness impregnation method. The preparation procedure consists of: (i) impregnation of Ambersorb-563 activated carbon (Rohm and Haas Co.) with an aqueous solution of PdCl$_2$.2H$_2$O/HCl, (ii) calcinations of the impregnated catalyst in flowing air with a temperature program of 3° C./min from 298 K to 573 K and 10 hours at 573 K, (iii) impregnation of the Pd/C with an aqueous solution of NaI, and (iv) then drying overnight in air at the room temperature.

Figure 5:
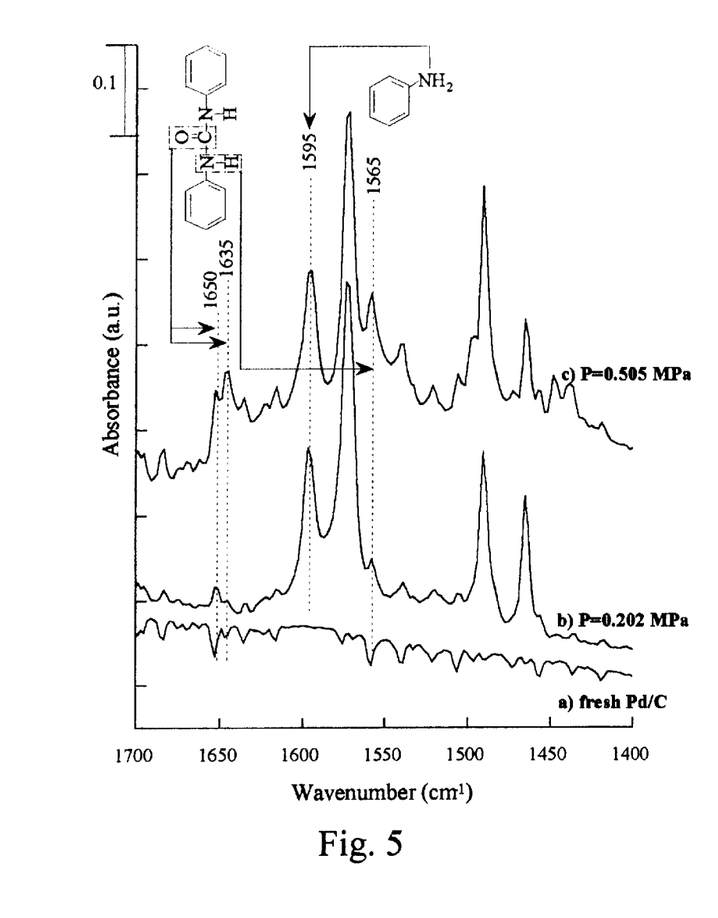
FIG. 5 is an IR spectra evidencing the production of carbamate according to Example 4 of the present invention, 5 wt % Pd-2.5% NaI/C as the catalytic system.
Figure 6:
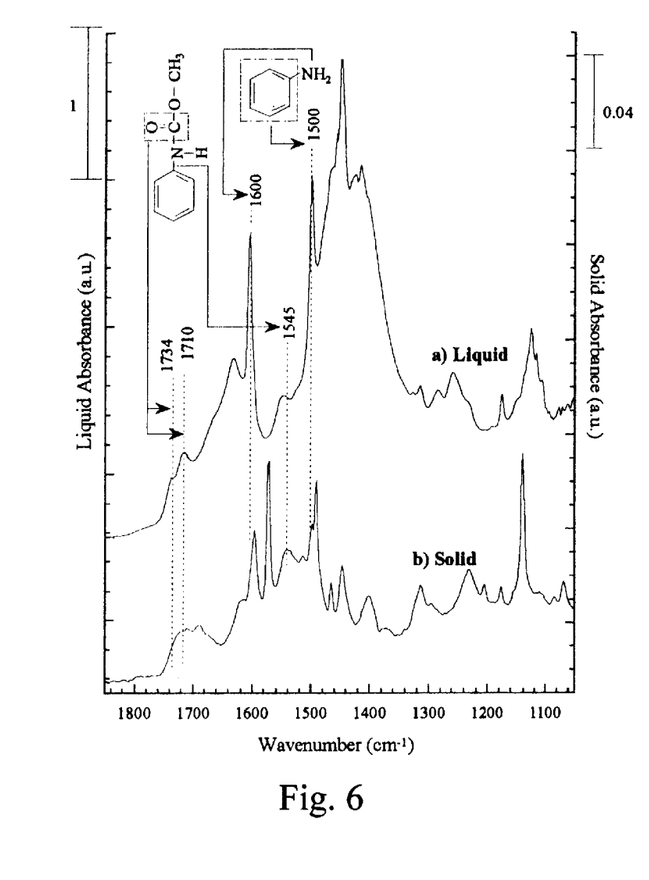
FIG. 6 is an IR spectra also evidencing the production of carbamate according to Example 4 of the present invention.

Seven hundred mg of Pd—NaI/C was placed in a tubular reactor with the glass wool packed at both ends. The catalyst was exposed to a flow of CO/O$_2$/methanol/aniline (molar ratio: 18.6/1.86/47.9/1) at 20 cm$^3$/min for 5 min. The reaction was allowed to occur in a batch mode at 373 K and 0.202 MPa for 1 h to produce diphenylurea. Following 1 hour of the reaction, the reactor was cooled down and the catalyst was removed for analysis by diffuse reflectance infrared Fourier transform spectroscopy (DRIFT). The sample showed a weak C=O band at 1635–1650 cm$^{-1}$ and a N—H band at 1565 cm$^{-1}$, indicating the formation of diphenylurea (FIG. 5(b)). Increasing the reaction pressure on the fresh catalyst to 0.505 MPa increased the formation of diphenylurea as evidenced by the prominent IR peaks at 1635, 1650, and 1565 cm$^{-1}$ as shown in FIG. 5(c). Following the synthesis of diphenylurea at 0.505 MPa, the reaction temperature was raised to 438 K for 1 h to produce methyl-N-phenyl carbamate. The product was flushed out by CO at 295 K for GC and IR analysis. The collected liquid product exhibits an IR spectrum, which consists of carbamate C=O band at 1734 and 1710 cm$^{-1}$ as shown in FIG. 6(a). GC analysis showed the methanol/aniline/carbamate molar fraction of 379.8/7.45/1 in the liquid product. Part of carbamate remains on the catalyst surface as shown on the DRIFTS spectra in FIG. 6(b).

EXAMPLE 5

Heterogeneous gas-solid oxidative carbonylation reactions were carried out at 438 K for 2 h in an autoclave with CO/O$_2$/methanol/aniline/NaI. The molar ration of CO to O$_2$ is 10:1. The catalysts listed in Table 1 were prepared by impregnation. Products were analyzed to determine the compositions by GC as shown in Table 1. 0.250 g of each of the catalysts was employed. 0.042 g of NaI was used with each catalyst. 1.84 g of aniline and 8.54 g of methanol were employed.

TABLE 1

Reactant Conversion and Product Yield For Selected Catalyst Systems Under Various Reaction Conditions

| Catalyst | Reaction Conditions | Reactant Conversion (%) | | Product Yield (%) |
|---|---|---|---|---|
| | | $C_6H_5$—$NH_2$ | $CH_3OH$ | $C_6H_5$—NH—COO—$CH_3$ |
| 5.0 wt % $CuCl_2$/HZSM-5 | 0.101[a]/1.156[b] MPa, 438 K | 43.5 | 6.8 | 2.0 |
| | 3.792/5.442 MPa, 438 K | 45.7 | 8.6 | 22.8 |
| 4.7 wt % $CuCl_2$— | 0.101/1.020 MPa, 438 K | 70.8 | 9.7 | 4.4 |
| 4.4% $PdCl_2$/HZSM-5 | 3.792/5.238 MPa, 438 K | 95.2 | 14.7 | 90.1 |
| 4.4 wt % $PdCl_2$/HZSM-5 | 0.101/1.170 MPa, 438 K | 37.4 | 6.3 | 1.8 |
| | 3.792/5.413 MPa, 438 K | 50.4 | 8.4 | 27.4 |

[a]initial pressure
[b]final pressure

What is claimed is:

1. A gas-solid carbonylation process for the production of carbamate ester comprising the steps of:
    reacting gaseous amine, gaseous alcohol, gaseous oxygen, and gaseous carbon monoxide in the presence of a solid catalytic system including at least one catalyst of the formula $M_nX_m$ and at least one alkali salt of the formula AZ, wherein M is copper or Group VIII metal, X is a halogen or oxygen, n and m are whole numbers dependent upon the balancing of the valence numbers of M and X, A is an alkali metal, and Z is a halogen.

2. The process of claim 1, wherein said step of reacting is carried out in a continuous mode.

3. The process of claim 2, wherein said step of reacting is carried out in a continuous reactor selected from the group consisting of fixed bed reactors, slurry bubble column reactors, and continuously stirred tank reactors.

4. The process of claim 1, wherein said step of reacting is carried out in a batch mode.

5. The process of claim 4, wherein said step of reacting is carried out in a batch reactor selected from the group consisting of autoclaves and batch mixing tank reactors.

6. The process of claim 1, wherein the solid catalytic system is supported on a catalyst support.

7. The process of claim 6, wherein the catalyst support is selected from the group consisting of activated carbon, polymer supports, mesoporous materials, metal oxides.

8. The process of claim 6, wherein the catalyst support is selected from the groups consisting of activated carbon, polystyrene, poly(styrene-divinylbenzene), polyimide, zeolite, synthesized silicate material, MgO, $SiO_2$, $Al_2O_3$, $TiO_2$, and $V_2O_3$.

9. The process of claim 1, wherein said step of reacting is carried out at a temperature of from about 323 K to about 543 K.

10. The process of claim 1, wherein said step of reacting is carried out at a pressure of from about 0.1 MPa to about 10 MPa.

11. The process of claim 1, wherein the gaseous amine is selected from the group consisting of aliphatic amines having from about 1 to 16 carbon atoms, and aromatic amines having from 6 to 12 carbon atoms in an aromatic ring.

12. The process of claim 1, wherein the gaseous amine is selected from the group consisting of aniline, 1,2-diaminobenzene, 1,4 diaminobenzene, isomers of chloroaniline, 3,4 dichloroaniline, 4-isopropyl aniline, p-toluidine, chlorotoluidine, xylidine, alkoxyanilines, isomers of nitroaniline, 2,3-diaminotoluene, 2-amino-4-nitrotoluene, 2-amino-3 nitrotoluene, 2-amino-5-nitrotoluene, aminophenols, diaminoxylene, aminonitroxylenes, aminonaphthalenes, amino-anthracenes, chloraminobenzoic acids, aminobenzenesulfonic acids, 4,4-diaminodiphenylmethane, 2,2-diaminodiphenylmethane, 2,4-diaminodiphenylmethane, tris(4-aminophenyl) methane, aminopyridines, aminoquinolines, aminopyrroles, aminofurans, aminothiophenes, and 2-aminobenzothiazoles.

13. The process of claim 1, wherein the gaseous alcohol is selected from alcohols having from 1 to 16 carbon atoms and from 1 to 3 hydroxyl groups.

14. The process of claim 1, wherein the gaseous alcohol is selected from methanol, ethanol, n-propanol, isopropanol, n-butanol, t-butanol, n-pentanol, n-hexanol, cyclohexanol, benzyl alcohol, ethylene glycol, diethylene glycol, propylene glycol, glycerol, and trimethylolpropane.

15. The process of claim 1, wherein said step of reacting is carried out below the saturated vapor pressures of the amine and alcohol.

\* \* \* \* \*